US00PP08972P

United States Patent [19]

van Andel

[11] Patent Number: Plant 8,972

[45] Date of Patent: Nov. 8, 1994

[54] MINI-SPRAY CARNATION PLANT NAMED STAVIOLET

[75] Inventor: Jacob van Andel, Aalsmeer, Netherlands

[73] Assignee: Van Staaveren, B.V., Aalsmeer, Netherlands

[21] Appl. No.: 98,842

[22] Filed: Jul. 29, 1993

Related U.S. Application Data

[63] Continuation of Ser. No. 770,403, Oct. 3, 1991, abandoned.

[51] Int. Cl.[5] ..... A01H 5/00

[52] U.S. Cl. ..... Plt./70.2

[58] Field of Search ..... Plt. 70.1, 70.2, 70.6

*Primary Examiner*—Howard J. Locker

*Attorney, Agent, or Firm*—Tilton, Fallon, Lungmus & Chestnut

[57] ABSTRACT

A new and original mini-spray carnation plant particularly distinguished by its bright flat cyclamen purple flowers having white centers and deeply serrated white margins, which are borne profusely and intermittently in clusters on erect stems branching from the main stem of an upright bush that has a height of about 110 cm.

1 Drawing Sheet

This application is a continuation of application Ser. No. 07/770,403, filed Oct. 3, 1991, abandoned.

BACKGROUND OF THE NEW PLANT

This new mini-spray carnation plant originated as a sport of the variety Statropur (U.S. Plant Pat. No. 7,849) being grown at our nursery in Aalsmeer, Holland. This particular sport was discovered by me and attracted my attention because of its unusual flat cyclamen purple and white flowers and the apparent overall high quality of the plant growth. The new carnation is a sport of unknown causation. Staviolet differs from the parental cultivar in the color of its petals, its overall plant height, and in its fruit fertility. Listed below in Table 1 is a comparison of Staviolet with Statropur and other known sports of Statropur. The other sports provided in Table 1 are subjects of copending applications. Serial numbers for these applications are provided for in the Table.

TABLE 1

| | STAVIOLET | STATROPUR |
|---|---|---|
| SERIAL NO.: | 08/098,842 | 07/611,504 |
| RELATED APPLICATIONS: | 08/098,842 is a Continuation of 07/770,403 (Abandoned) | — |
| PATENT NO.: | — | U.S. Plant Pat. No. 7,849 |
| PETAL BODY: | RHS 74-A | RHS 74-B |
| PETAL BASE: | RHS 155-D | White |
| REVERSE SIDE: | RHS 155-D | White |
| STIGMA: | RHS 155-D | White |
| STYLE: | RHS 155-D | White |
| HEIGHT: | 100–110 cm. (average) | 150 cm. (average) |
| DISCOLORATION AFTER FULL BLOOM: | Slight | None |
| FERTILE FRUIT: | No | Yes |
| | STAGILAC | STAGIBORD |
| SERIAL NO.: | 08/099,271 | 08/100,073 |
| RELATED APPLICATIONS: | 08/099,271 is a Continuation of 07/756,798 (Abandoned) | 08/100,073 is a Continuation of 07/770,401 (Abandoned) |
| PATENT NO.: | — | — |
| PETAL BODY: | RHS 74-B | RHS 57-B + RHS 57-A ("Mottled Portion") |
| PETAL BASE: | RHS 155-D | RHS 155-D |
| REVERSE SIDE: | RHS 72-C | RHS 62-A |
| STIGMA: | RHS 155-D | RHS 64-B |
| STYLE: | RHS 155-D | RHS 64-B |
| HEIGHT: | 100–110 cm. (average) | 100–120 cm. (average) |
| DISCOLORATION AFTER FULL BLOOM: | Slight | Slight |
| FERTILE FRUIT: | No | No |
| | STAGIROS | |
| SERIAL NO.: | 08/099,780 | |
| RELATED APPLICATIONS: | 08/099,780 is a Continuation of 07/770,402 (Abandoned) | |
| PATENT NO.: | — | |
| PETAL BODY: | RHS 73-A + RHS 73-D ("Mottled Portion") | |
| PETAL BASE: | RHS 155-D | |
| REVERSE SIDE: | RHS 73-D | |
| STIGMA: | RHS 155-D | |
| STYLE: | RHS 155-D | |
| HEIGHT: | 100 cm. (average) | |
| DISCOLORATION AFTER FULL BLOOM: | Slight | |
| FERTILE FRUIT: | No | |

Asexual propagation of this plant was done by means of cuttings under my direction at Aalsmeer; and propagation of this new plant was continued through successive generations to determine whether the nvel characteristics of the parent plant would be retained from generation to generation and whether its momogeneity could be assured. This proved to be successful and this new carnation is now being propagated at Aalsmeer.

DESCRIPTION OF THE DRAWING

My new carnation cultivar is illustrated by the accompanying full-color photographic drawing, which shows blooming portions of spray stems with buds and flowers in several stages of development, the color rendition being as nearly true to that herein specified as is reasonably possible to obtain by professional photographic procedures.

DESCRIPTION OF THE NEW PLANT

The following is a detailed description of my new mini-spray carnation variety based upon observation of plants grown in greenhouse as well as outdoors at Aalsmeer and blooming during the current year. The color designations stated herein are according to The R.S.H. Colour Chart published by The Royal Horticultural Society of London, England.

THE PLANT

Origin: Sport.
Parentage:
*Statropur.*—U.S. Plant Pat. No. 7,849.
Classification:
*Botanic.*—Dianthus Hybrid.
*Commercial.*—Mini-spray carnation.
Form: Strong, upright bush.
Height: About 100–110 cm. in average.
Main Stem:
*Length.*—In average, about 100 cm.
*Growth habit.*—Strong, upright and fast.
*Branching Character.*—The main stem has 7–8 side branches and each side branch has 2–4 branches and each of these branches has 1–2 branches.
Foliage:
Quantity: Medium.
*Number of leaves.*—22–26.
*Leaf size.*—Length: 7–11 cm. Width: 1–2 cm.
*Leaf shape.*—Elliptical. Margins: Straight and entire. Texture: Smooth. Color: Upper side — R.H.S. 137-A. Under side — R.H.S. 137-C.

THE BUD

Size: Medium.
*Diameter.*—Averaging about 3 mm.
*Length.*—Averaging about 20 mm.
Shape: Cylindrical, long and pointed.
Calyx:
*Shape.*—Cylindrical. The calyx is formed out of 5 pointed sepals of about 5 mm. which are joined at the lower point and sharply pointed at the apex.
*Size.*—Averaging 3 mm in width and 20 mm in length.
*Splitting.*—The calyx does not split.
*Aspect.*—Smooth.
*Color.*—R.H.S. 137-D.
Flower Stem:
*Character.*—Erect.
*Color.*—137-C.
*Length.*—80 to 110 cm.

THE FLOWER

Blooming habit: Intermittent and profuse, from Spring through Fall.
Size of flower: Small.
*Diameter.*—Averaging about 30 mm.
*Depth.*—Averaging about 5 mm.
Borne: In a cluster.
Shape when first opening: Flat.
When mature: Flat.
Petalage:
*Number of petals.*—5.
*Arrangement.*—Side by side around the pistil.
*Texture.*—Soft.
*Appearance.*—Velvety.
*Apex margin.*—Deeply serrated and white portions covering about one third of the petal length.
*Color.*—Outer portion and inner portion of the petals: Body: R.H.S. 74-A. In this "body" there are 50–100 scattered small spots which have a color of R.H.S. 155-D. The deeply serrated margin also has a color of R.H.S. 155-D. Base: R.H.S. 155-D. Reverse Side: R.H.S. 155-D. Discoloration after full bloom: Slight.
Persistence: The flowers hang on and dry.
Fragrance: Yes.
Disease resistance: Resistant to *Fusarium oxysporum*, as observed at Aalsmeer.
Lasting quality: Averaging about 12 days as a cut flower and 21 days on the plant.
Changes with maturity: The color of the bud and the color of the petal when they first begin to show is R.H.S. 74-A at the body and R.H.S. 155-D at the base. When the flower matures, the color of the petal turns to R.H.S. 74-B and when the flower is old, the color turns to R.H.S. 74-C.

REPRODUCTIVE ORGANS

Stamens: None.
Anthers: None.
Filaments: None.
Pistils:
*Number.*—1.
*Styles.*—Length: 22 mm, in average. Color: White.
*Stigmas.*—Color: White.

FRUIT

Fertility: The fruit is not fertile.
Shape: Pear-shaped.

I claim:

1. The new and distinctive mini-spray carnation plant, substantially as herein shown and described, particularly characterized by its small flat cyclamen-purple flowers having petals with a deeply serrated white margins and wide white base and having flowers produced profusely in clusters on strong, upright branches of the main stem of a fast-growing, tall, erect bush.

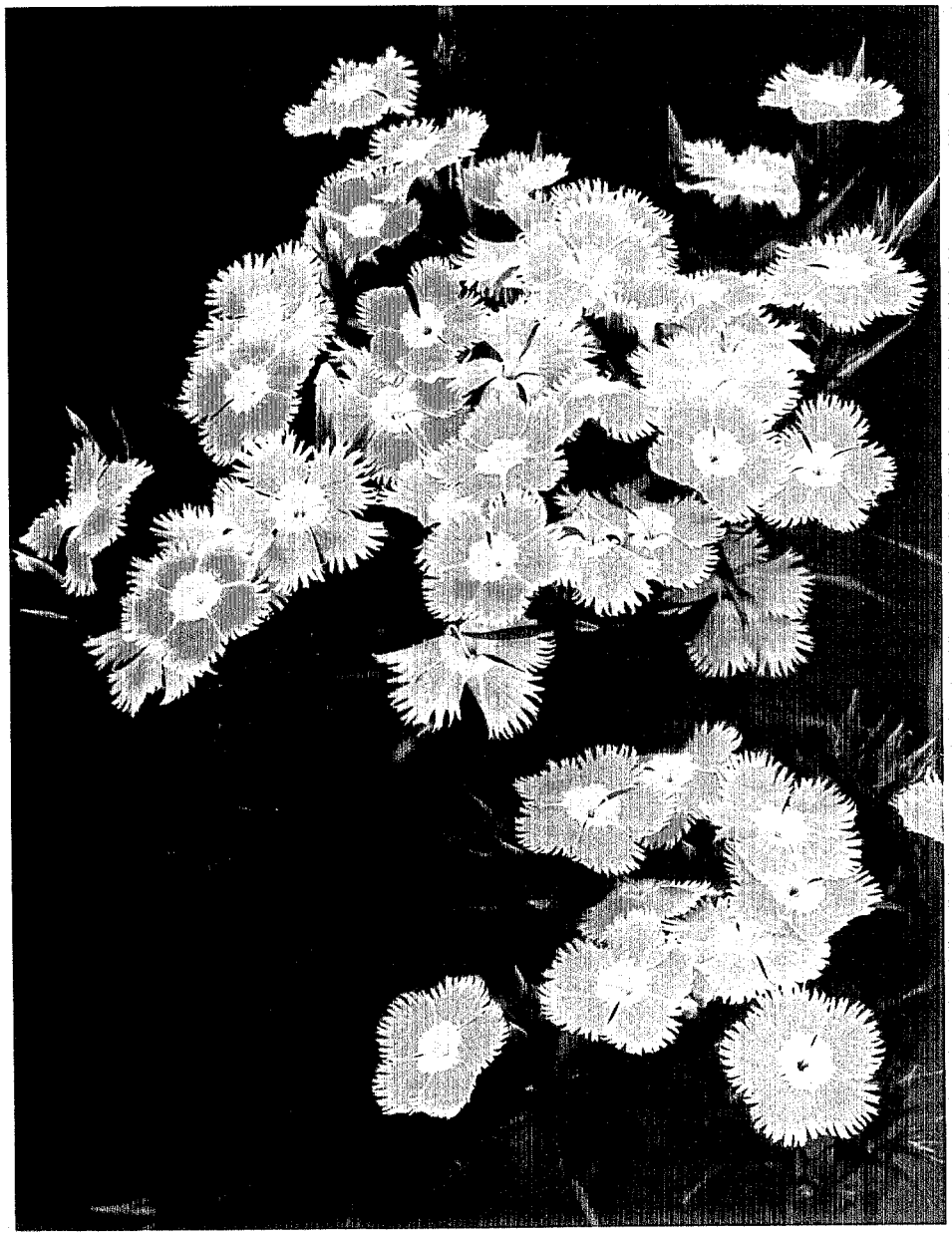

* * * * *